United States Patent [19]

Himmler et al.

[11] Patent Number: 4,990,647
[45] Date of Patent: Feb. 5, 1991

[54] PROCESS FOR THE PREPARATION OF UNSYMMETRIC BIARYL COMPOUNDS

[75] Inventors: Thomas Himmler, Cologne; Rudolf Braden, Odenthal-Scheuren, both of Fed. Rep. of Germany

[73] Assignee: Bayer Aktiengesellschaft, Leverkusen, Fed. Rep. of Germany

[21] Appl. No.: 342,501

[22] Filed: Apr. 24, 1989

[30] Foreign Application Priority Data

May 11, 1988 [DE] Fed. Rep. of Germany ....... 3816120

[51] Int. Cl.$^5$ .................... C07C 253/14; C07D 207/34
[52] U.S. Cl. ...................................... 558/414; 548/453; 548/517; 548/518; 548/526; 548/527; 548/531; 548/532; 549/50; 549/60; 549/364; 549/414; 549/435; 549/436; 549/466; 549/468; 549/473; 560/102; 568/425
[58] Field of Search .................... 560/102; 558/414; 568/642; 585/425; 548/453, 517, 518, 526, 527, 531, 532; 549/50, 60, 364, 414, 435, 436, 466, 468, 473

[56] References Cited

PUBLICATIONS

Tsou and Kochi, *JACS*, 101, pp. 7547–7560, (1979).
Colon et al., *J. Org. Chem.*, vol. 51, pp. 2627–2637, (1986).
Semmelhack et al., *JACS*, 93:22, pp. 5908–5910, (1971).
Coffen et al., *J. Org. Chem.*, vol. 49, pp. 296–300, (1984).
Negishi et al., *J. Org. Chem.*, vol. 42, pp. 1821–1823, (1977).

*Primary Examiner*—Joseph P. Brust
*Assistant Examiner*—Jacqueline Haley
*Attorney, Agent, or Firm*—Sprung Horn Kramer & Woods

[57] ABSTRACT

Unsymmetric biaryl compounds are prepared by coupling two different halogenoaromatics by reaction with a metal and carrying out the reaction in the presence of catalytic amounts of a nickel compound, a promoter and a phosphorus-containing ligand.

13 Claims, No Drawings

PROCESS FOR THE PREPARATION OF UNSYMMETRIC BIARYL COMPOUNDS

The present invention relates to a process for the preparation of unsymmetric biaryl compounds from a chloroaromatic and a halogenoaromatic.

Unsymmetric biaryl compound are of industrial interest as precursors for brighteners, pharmaceuticals, plant protection active compounds and liquid crystal materials.

T. T. Tsou et al., J.A.C.S, 101, 7547-7560 (1979) report the occurrence of unsymmetric biaryl compounds when two different aryl bromides or aryl iodides are coupled with metallic zinc and catalytic amounts of a nickel compound. The transfer of this reaction to the less reactive chloroaromatics and positive influences by promoters cannot be deduced from this publication.

EP-A-0,012,201 describes the preparation of symmetric biaryl compounds by coupling of two identical chloroaromatics with metallic zinc in the presence of nickel, promoters and phosphorus-containing ligands. In a parallel publication by the same authors (see J. Org. Chem. 51, 2627-2637 (1986)), it is expressly stated that this process is unsuitable for the preparation of unsymmetric biaryl compounds.

A process has now been found for the preparation of unsymmetric biaryl compounds, which is characterized in that an optionally substituted chloroaromatic is coupled with a differently substituted iodo-, bromo- or chloroaromatic by reaction with a metal and the reaction is carried out in the presence of catalytic amounts of a nickel compound, a promoter and a phosphorus-containing ligand. The differently substituted iodo-, bromo- pr chloroaromatic is preferably likewise a chloroaromatic.

In the process according to the invention, it is possible to use, for example, halogenoaromatics of the formula (I)

Ar-Hal    (I)

in which

Hal represents iodine, bromine or chlorine and

Ar represents an optionally substituted aromatic carbocyclic hetero atoms containing ring having 5 or 6 ring-forming atoms. Examples of possible hetero atoms are nitrogen and/or phosphorus atoms. Preferred hetero atoms containing aromatic rings having 5 or 6 ring-forming atoms contain 1 or 2 nitrogen atoms.

Preferred compounds of the formula (I) are those of the formulae (II), (III) or (IV)

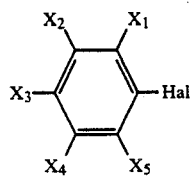
(II)

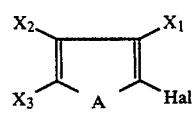
(III)

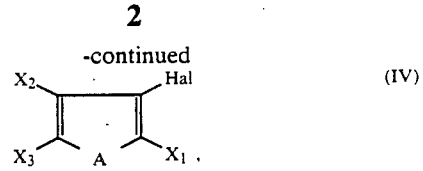
(IV)

in which

Hal represents iodine, bromine or chlorine and $X_1$ and $X_5$ can be identical or different and independently of one another represent hydrogen, $C_1$- to $C_6$-alkyl, optionally substituted $C_6$- to $C_{14}$-aryl, fluorine, $C_1$- to $C_6$-alkoxy, $C_1$- to $C_6$-alkylthio, $C_1$- or $C_2$-halogenoalkyl having 1 to 5 halogen atoms, $C_1$- or $C_2$-halogenoalkoxy having 1 to 5 halogen atoms, optionally substituted $C_6$- to $C_{14}$-phenoxy, $C_1$- to $C_{18}$-alkylamino, $C_2$- to $C_{36}$-dialkylamino, $C_6$- to $C_{14}$-arylamino, $C_{12}$- to $C_{18}$-diarylamino, $C_2$- to $C_{18}$-carboxyalkyl, $C_7$- to $C_{10}$-carboxyaryl, formyl, cyano, $C_1$- to $C_{18}$-alkylsulphinyl, $C_1$- to $C_{18}$-alkylsulphonyl, $C_6$- to $C_{14}$-arylsulphinyl, $C_6$- to $C_{14}$-arylsulphonyl, OCO—$C_1$- to $C_{18}$-alkyl or OCO—$C_6$- to $C_{14}$-aryl, wherein OCO—$C_1$- to $C_{18}$-alkyl and OCO—$C_6$- to $C_{14}$-aryl radicals cannot be in the ortho-position relative to the halogen atom and wherein any two adjacent radicals from the group $X_1$ to $X_5$ together can also represent one of the groupings: —CH$_2$—CH$_2$—CH$_2$—, —CH$_2$—CH$_2$—CH$_2$—CH$_2$—, —CH=CH—CH$_2$—, —CH=CH—CH=CH—, —O—CH$_2$—O— or —O—CH$_2$—CH$_2$—O—, in which in each case one or more or all of the hydrogen atoms can optionally be substituted by fluorine and one or more or all of the hydrogen atoms of the groupings —CH$_2$—CH$_2$—CH$_2$— and —CH$_2$—CH$_2$—CH$_2$13 CH$_2$13 can optionally also be substituted by chlorine, and A represents oxygen, sulphur or NR, where R=$C_1$- to $C_{10}$-alkyl, benzyl, optionally substituted phenyl having 6 to 20 C atoms, formyl or acetyl.

Further preferred halogenoaromatics are those of the formula (II) in which at least $X_1$ or $X_5$ represents hydrogen, and those of the formula (IV) in which at least $X_1$ or $X_2$ represents hydrogen.

$X_1$ to $X_5$ are preferably identical or different and independently of one another represent hydrogen, $C_1$- to $C_4$-alkyl, $C_6$- to $C_{10}$-aryl which is optionally substituted by fluorine, cyano, $C_1$- to $C_4$-alkyl, acetoxy, $C_1$- to $C_3$-carboxyalkyl or $C_1$- or $C_2$-halogenoalkyl having 1 to 5 halogen atoms, in particular fluorine atoms, fluorine, $C_1$- to $C_4$-alkoxy, $C_1$- to $C_4$-alkylthio, $C_1$- to $C_2$-halogenoalkyl having 1 to 5 fluorine and/or chlorine atoms, $C_1$- to $C_2$-halogenoalkoxy having 1 to 5 fluorine and/or chlorine atoms, phenoxy which is optionally substituted by fluorine, cyano, $C_1$- to $C_4$-alkyl, acetoxy, $C_2$- to $C_3$- carboxyalkyl or $C_1$- or $C_2$-halogenoalkyl having 1 to 5 halogen atoms, in particular fluorine atoms, $C_1$- to $C_4$-alkylamino, $C_2$- to $C_8$-dialkylamino, $C_7$- to $C_{10}$-arylamino, $C_{12}$- to $C_{16}$-diarylamino, $C_2$- to $C_6$-carboxyalkyl, $C_7$- to $C_8$-carboxyaryl, formyl, cyano, $C_1$- to $C_6$-alkylsulphinyl, $C_1$- to $C_6$-alkylsulphonyl, $C_6$- to $C_{10}$-arylsulphinyl, $C_6$- to $C_{10}$-arylsulphonyl, OCO—$C_1$- to $C_6$-alkyl or OCO—$C_6$- to $C_{10}$-aryl, the limitations described above likewise applying to the two radicals last mentioned, and wherein any two adjacent radicals from the group $X_1$ to $X_5$ together also represent one of the groupings —CH$_2$—CH$_2$—CH$_2$—CH$_2$—,
—CH=CH—CH=CH—or
—O—CH$_2$—CH$_2$—O— which are preferably unsubstituted.

Particularly preferably, $X_1$ to $X_5$ are identical or different and represent hydrogen, phenyl which is optionally substituted by fluorine, cyano, acetoxy or $C_2$- to $C_3$-carboxyalkyl, fluorine, $C_1$- to $C_4$-alkoxy, $C_1$- or $C_2$-halogenoalkyl having 1 to 5 halogen atoms, in particular fluorine atoms, $C_2$- to $C_8$-dialkylamino, $C_2$- to $C_6$-carboxyalkyl, formyl, cyano or OCO—$C_1$- to $C_6$-alkyl.

Other preferred compounds of the formulae (II), (III) and (IV) contain as $X_1$ to $X_5$ only hydrogen atoms or 1 or 2 radicals or groupings other than hydrogen.

In the formulae (III) and IV), A preferably represents sulphur or NR, where R=$C_1$- to $C_6$-alkyl, benzyl, optionally substituted phenyl having 6 to 12 C atoms, formyl or acetyl.

The compounds of the formula (II) are preferable to the compound of the formulae (III) and (IV).

A chloroaromatic and a differently substituted halogenoaromatic, wherein halogen represents iodine, bromine or chlorine, are used in the process according to the invention and a biaryl compound containing the two different aromatic, radicals is obtained therefrom. For example, the process according to the invention can be illustrated with the aid of the following reaction equation:

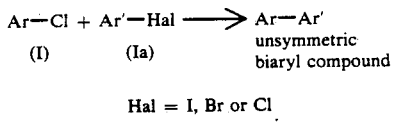

Ar—Cl + Ar'—Hal ⟶ Ar—Ar'
(I)    (Ia)    unsymmetric biaryl compound

Hal = I, Br or Cl

Ar and Ar' have the meaning given above for Ar, but within which Ar and Ar' differ from one another.

The two different halogenoaromatics can be used in equimolar amounts. It is often also advantageous to use one of the two halogenoaromatics in excess, because the halogenoaromatic used in less than the equimolar amount is then generally reacted more selectively to give the unsymmetric biaryl compound desired. The choice of the halogenoaromatic used in excess can be made on the basis of various criteria. For example, it is possible to use in excess the halogenoaromatic which is more easily and/or cheaply accessible or the halogenoaromatic of which the corresponding symmetric biaryl compound formed as a byproduct can be removed more easily from the reaction mixture. The halogenoaromatic used in excess can be employed, for example, in an amount of 110 to 1,000 mol %, based on the other chloroaromatics. This amount is preferably 150 to 500 mol %, particularly preferably 200 to 400 mol %.

The halogenoaromatics used are preferably anhydrous.

Possible metals for coupling the two halogenoaromatics are, in particular, zinc, manganese and magnesium. Zinc is preferred, in particular in the form of zinc powder, which is particularly preferably used in purified form. The purification can be carried out, for example, by washing the zinc powder with glacial acetic acid, water and acetone in succession and then drying it in vacuo. The amount of this metal can vary within wide limits. For example, it is possible to use 0.5 to 10 mol equivalents of the metal, based on the sum of the two halogenoaromatics employed. This amount is preferably 0.5 to 5 mol equivalents.

Possible nickel compounds are, in particular, anhydrous nickel compounds in which the nickel is present in the oxidation level 0 or can be converted into the oxidation level 0 by reduction with zinc, manganese and/or magnesium. Examples which may be mentioned are: nickel(II) halides, such as nickel(II) chloride, nickel(II) bromide and nickel(II) iodide, nickel(II) sulphate, nickel(II) carbonate, nickel(II) salts of organic acids having 1 to 18 C atoms, such as nickel(II) acetate and nickel(II) propionate, nickel(II) complexes, such as nickel(II) acetylacetonate and dichloro-bis-(triphenylphosphine)-nickel(II), and nickel(0) complexes, such as bis-(cycloocta-1,5diene)-nickel(0) and tetrakis-(triphenylphosphine)-nickel(0). All these nickel compounds are commercially available or can be prepared in a known manner, and if appropriate are to be freed from bonded or adhering water in a known manner.

The nickel(II) halides mentioned in anhydrous form, in particular nickel(II) chloride, which is obtainable, for example, from $NiCl_2 \times 6H_2O$ by reaction with thionyl chloride, are preferred.

The nickel compound can be used, for example, in an amount of 0.1 to 25 mol %, based on the sum of the two halogenoaromatics employed. This amount is preferably 1 to 20 mol %, and particularly preferably 5 to 15 mol %. It is also possible to use mixtures of two or more nickel compounds.

Possible promoters are, in particular, alkali metal, alkaline earth metal, zinc, magnesium and manganese halides. The iodines are in each case preferred. The promoter or promoters can be used, for example, in amounts of 0.1 to 1,000 mol %, based on the nickel compound employed. This amount is preferably 1 to 700 mol %, particularly preferably 10 to 500 mol %.

Possible phosphorus-containing ligands are, in particular, triarylphosphines, for example those having 6 to 10 C atoms per aryl unit. Triphenylphosphine, the tritolylphosphines and trinaphthylphosphine are preferred. Triphenylphosphine is particularly preferred. The phosphorus-containing ligand or the phosphorus-containing ligands can be used, for example, in an amount of 200 to 10,000 mol %, based on the nickel compound employed. This amount is preferably 400 to 5,000 mol %, and particularly preferably 500 to 1,000 mol %.

If appropriate, one or more polycyclic, aromatic compounds having at least two nitrogen atoms in different aromatic rings and a total of 10 to 18 C atoms can be used in addition to phosphorus-containing ligands. Preferred compounds here are 2,2'-dipyridyl and 1,10-phenanthroline. Polycyclic aromatic compounds can be used, for example, in amounts of 50 to 500 mol %, based on the nickel compound employed.

The process according to the invention can be carried out in the presence or absence of solvents. It is preferably carried out in the presence of solvents, because, for example, the removal of the heat of reaction can then easily be controlled. Aprotic polar solvents, such as dimethylformamide, dimethylacetamide, N-methylcaprolactam, N-methyl-pyrrolidinone, dimethyl sulphoxide and tetramethylene sulphone are suitable. Solvents in dried form are preferably used, for example solvents treated with a molecular sieve and/or if appropriate solvents distilled in a protective gas atmosphere.

The process according to the invention can be carried out, for example, at temperatures from 0° to 250° C. Preferred temperatures are those from 20° to 200° C., in particular those from 50° to 150° C.

It is advantageous to carry out the reaction according to the invention in an inert protective gas atmosphere. Suitable protective gases are, for example, nitrogen, helium and argon.

The process according to the invention is in general carried out under normal pressure. However, it can also be carried out under increased or reduced pressure, for example in the range from 0.1 to 10 bar.

An example of an embodiment of the process according to the invention comprises a procedure in which the metal, the nickel compound, the promoter, the phosphorus-containing ligand, if appropriate a polycyclic aromatic compound and if appropriate a polar aprotic solvent are first mixed with one another, this mixture is initially introduced into the reaction vessel and the two halogenoaromatics are added to the mixture separately or as a mixture, if appropriate together with (further) solvent.

Examples of suitable reaction times for the reaction according to the invention are those in the range from 3 minutes to 24 hours. The reaction time is preferably between 0.1 and 10 hours, particularly preferably between 0.5 and 6 hours.

Working up of the reaction mixture can be carried out in various ways, by removing the metal salts, nickel compounds, ligands and by-products (for example symmetric biaryl compounds) contained therein and if appropriate the metals present and if appropriate the solvent present. Various methods of working up are preferred, depending on the nature and amount of these constituents. For example, it is possible first to filter the mixture, then to remove the solvent from the filtrate, if appropriate, by concentration in vacuo, subsequently to take up the residue in a water-immiscible solvent (for example of chlorinated hydrocarbon), to extract this organic phase with water or aqueous hydrochloric acid, to separate off the organic phase again and to concentrate it and if appropriate to further purify the residue then obtainable by recrystallization or chromatographic methods.

The process according to the invention enables unsymmetric biaryl compounds to be prepared in good yields and selectivities. This is exceptionally surprising in view of the prior art described above, since in the technical circles in question the view has to date been taken that unsymmetric biaryl compounds cannot be prepared in a useful manner starting from chloroaromatics. When the more reactive bromo- and iodoaromatics are used, it was to be expected that these preferentially react with themselves and reaction products with chloroaromatics cannot be obtained in a noticeable amount.

EXAMPLES

Example 1

Preparation of methyl 4-(3-trifluoromethylphenyl)-benzoate 33 g of zinc powder, 33 g of triphenylphosphine, 5 of sodium iodide, 2.2 g of nickel(II) chloride and 200 ml of dimethylformamide were mixed under a nitrogen atmosphere and the mixture was initially introduced into the reaction vessel. The mixture was kept at 50° to 60° C. for half an hour, after which a suspension coloured deep red-brown was present. A solution containing 20.2 g (0.11 mol) of 3-chloro-benzotrifluoride, 38.2 g (0.22 mol) of methyl 4-chloro-benzoate and 100 ml of dimethylformamide was added dropwise to this suspension in the course of half an hour. After 6 hours at 80° C., the reaction mixture was introduced into 500 ml of chloroform and filtered. The residue on the filter was boiled up in 400 ml of toluene and filtered off hot. After cooling, 15 g of dimethyl biphenyl-4,4'-dicarboxylate (50.5% of theory—based on the methyl 4-chloro-benzoate employed) of melting point 213° to 214° C. were obtained. The filtrate was extracted by shaking with dilute aqueous hydrochloric acid and with water and the organic phase was dried over sodium sulphate and concentrated. The resulting residue was distilled. 6.4 g of 3,3'-bis-(trifluoromethyl)-biphenyl (20% of theory—based on the 3-chloro-benzotrifluoride employed) and a total of 16 g of methyl 4-(3-trifluoromethylphenyl)-benzoate (52% of theory—based on the 3-chloro-benzotrifluoride employed) of boiling point 125° C. to 130° C. under 0.1 to 0.3 mbar were obtained in this manner.

Example 2

Preparation of methyl 4-(4-trifluoromethyl-phenyl)benzoate

The procedure was exactly as in Example 1, but instead of 3-chloro-benzotrifluoride the same amount of 4-chlorobenzotrifluoride was used. 16.5 g of methyl 4-(4-trifluoromethyl-phenyl)-benzoate were obtained in this manner. This corresponds to 53% of theory—based on the 4-chlorobenzotrifluoride employed.

Example 3

Preparation of 4-acetoxy-4'-methyl-biphenyl 20 g of zinc dust, 20 go of triphenylphosphine, 3 g of sodium iodide and 1.3 of nickel(II) chloride in 150 ml of dimethylformamide were initially introduced into the reaction vessel under a nitrogen atmosphere. The mixture was kept at 60° C. for half an hour. A solution containing 12.3 g (0.1 mol) of 4-chlorotoluene, 17.1 g (0.1 mol) of 4-chloroacetoxybenzene and 50 ml of dimethylformamide was then added dropwise. After 6 hours at 80° C., the reaction mixture was filtered, the filtrate was concentrated, the residue was dissolved in 500 ml of chloroform and the mixture was extracted by shaking with water. After drying the organic phase over sodium sulphate and stripping off the solvent, the oily residue was analyzed by gas chromatography. The yield of 4-acetoxy-4'-methylbiphenyl was 40% of theory.

Example 4

Preparation of 4-methoxy-4'-methyl-biphenyl

The procedure was exactly as described in Example 3, but instead of 4-chloroacetoxybenzene 14.3 g (0.1 mol) of 4-chloroanisole was employed. 4-Methoxy-4'-methyl-biphenyl became in a yield of 49% of theory, according to analysis by gas chromatography.

Example 5

Preparation of 4-acetoxy-4'-cyano-biphenyl

The procedure was exactly as described in Example 3, but instead of 4-chlorotoluene a corresponding amount of 4-chloro-benzonitrile was employed. 4-Acetoxy-4'-cyanobiphenyl became in a yield of 42% of theory, according to analysis by gas chromatography.

What is claimed is:

1. A process for the preparation of unsymmetric biaryl compounds, in which a chloroaromatic compound is coupled with a differently substituted iodo-, bromo- or chloroaromatic compound, said chloroaromatic compound and said differently substituted aromatic compound are a halogenoaromatic selected from the group consisting of

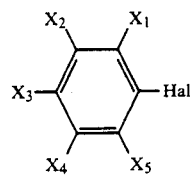  (II)

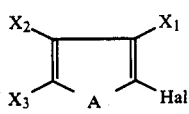  (III)

and

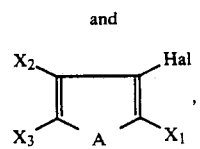  (IV)

in which
Hal represents chlorine for the chloroaromatic compound and iodine, bromine or chlorine for the differently substituted aromatic compound, and
$X_1$ to $X_5$ are identical or different and independently of one another represent hydrogen, $C_1$- to $C_6$-alkyl, $C_6$- to $C_{14}$-aryl, fluorine, $C_1$- to $C_6$-alkoxy, $C_1$- to $C_6$-alkylthio, $C_1$- or $C_2$- fluoroalkyl having 1 to 5 fluorine atoms, $C_1$- or $C_2$- fluoroalkoxy having 1 to 5 fluoro atoms, phenoxy, $C_1$- to $C_{18}$-alkylamino, $C_2$- to $C_{36}$-dialkylamino, $C_6$- to $C_{14}$-arylamino, $C_{12}$- to $C_{18}$-diarylamino, $C_2$- to $C_{18}$-carboxyalkyl, $C_7$- to $C_{10}$-carboxyaryl, formyl, cyano, $C_1$- to $C_{18}$-alkylsulphinyl, $C_1$- to $C_{18}$-alkylsulphonyl, $C_6$- to $C_{14}$-arylsulphinyl, $C_6$- to $C_{14}$-arylsulphonyl, OCO—$C_1$- to $C_{18}$-alkyl or OCO—$C_6$- to $C_{14}$-aryl, wherein OCO—$C_1$- to $C_{18}$-alkyl and OCO—$C_6$- to $C_{14}$-aryl radicals cannot be in the orthoposition relative to the halogen atom and wherein any two adjacent radicals from the group $X_1$ to $X_5$ together can also represent one of the groupings —$CH_2$—$CH_2$—$CH_2$—, —$CH_2$—$CH_2$—$CH_2$—$CH_2$—, —$CH$=$CH$—$CH_2$—, —$CH$=$CH$—$CH$=$CH$—, —O—$CH_2$—O— or —O—$CH_2$—$CH_2$—O—, in which in each case one or more or all of the hydrogen atoms may or may not be replaced by fluorine, one or more or all of the hydrogen atoms of the groupings —$CH_2$—$CH_2$—$CH_2$— and $CH_2$—$CH_2$—$CH_2$13 $CH_2$ may or may not be replaced by chlorine and
A represents oxygen, sulphur or NR, where R=$C_1$- to $C_{10}$-alkyl, benzyl, phenyl having 6 to 20 C atoms, formyl or acetyl, comprising reacting the chloroaromatic compounds with a metal in the presence of a catalytic amount of a nickel compound selected from the group consisting a nickel (II) halide, a nickel (II) slat of an organic acid having 1 to 18 carbon atoms, a nickel (II) complex and a nickel (O) complex, said catalytic amount of nickel compound being 0.1 to 25 mole % based on the sum of the two halogenoaromatics, a promoter selected from the group consisting of halides of alkali metals, alkaline earth metals, zinc, magnesium and manganese and a phosphorous-containing ligand and wherein the reaction is conducted at a temperature of 0° to 250° C. and at a pressure of 0.1 to 1 bar, whereby the desired product is obtained in a yield of at least about 40%.

2. A process according to claim 1, in which one of the halogenoaromatics is used in an amount of 110 to 1,000 mol %, based on the other chloroaromatic.

3. A process according to claim 1, in which zinc, manganese and/or magnesium in an amount of 0.5 to 10 mol equivalents, based on the sum of the two halogenoaromatics, are used as the metal for coupling the two different halogenoaromatics.

4. A process according to claim 1, in which the alkali metal, alkaline earth metal, zinc, magnesium and/or manganese halides are used as promoters in an amount of 0.1 to 1,000 mol %, based on the nickel compound employed.

5. A process according to claim 1, in which triarylphosphines are used as phosphorus-containing ligands in an amount of 200 to 10,000 mol %, based on the nickel compound employed.

6. A process according to claim 1, in which said promoter contains one or more polycyclic aromatic compounds having at least two nitrogen atoms n different aromatic rings and a total of 10 to 18 C atoms are used in an amount of 50 to 500 mol %, based on the nickel compound employed, in addition to phosphorous-containing ligands.

7. A process according to claim 1, which is carried out in the presence of an aprotic polar solvent.

8. A process according to claim 1, wherein for $X_1$ to $X_5$, the aryl is unsubstituted or substituted by fluorine, cyano, $C_1$-$C_4$-alkyl, acetoxy, $C_2$-$C_3$-carboxyalkyl or $C_1$14 $C_2$-halogenoalkyl having 1 to 5 halogen atoms.

9. A process according to claim 1, wherein for $X_1$ to $X_5$, the phenoxy is unsubstituted or substituted by fluorine, cyano, $C_1$-$C_4$-alkyl, acetoxy, $C_2$-$C_3$-carboxyalkyl or $C_1$14 $C_2$-halogenoalkyl having 1 to 5 halogen atoms.

10. A process according to claim 1, wherein the nickel compound is nickel (II) chloride, nickel (II) bromide, nickel (II) iodine, nickel (II) sulphate, nickel (II) carbonate, nickel (II) acetate, nickel (II) propionate, nickel (II) acetylacetonate, dichloro-bis(triphenylphosphine)-nickel (II), bis(-cycloocta-1,5-diene)-nickel (O) or tetrakis - (triphenylphosphine)-nickel (O).

11. A process according to claim 1, wherein the phosphorous-containing ligand is triphenylphosphine, tritolylphosphine or trinaphthylphosphine.

12. A process according to claim 1, wherein said amount of nickel is 1 to 20 mole %, based on the sum of the two halogenoromatics.

13. A process according to claim 1 , wherein said amount of nickel is 5 to 15 mole %, based on the sum of the two halogenoromatics.

* * * * *